United States Patent
Höynälä

(10) Patent No.: US 11,317,859 B2
(45) Date of Patent: May 3, 2022

(54) SYSTEM FOR DETERMINING SOUND SOURCE

(71) Applicant: KIPUWEX OY, Oulu (FI)

(72) Inventor: Marko Höynälä, Oulu (FI)

(73) Assignee: KIPUWEX OY, Oulu (FI)

( * ) Notice: Subject to any disclaimer, the term of this patent is extended or adjusted under 35 U.S.C. 154(b) by 152 days.

(21) Appl. No.: 16/651,655

(22) PCT Filed: Sep. 26, 2018

(86) PCT No.: PCT/FI2018/050693
§ 371 (c)(1),
(2) Date: Mar. 27, 2020

(87) PCT Pub. No.: WO2019/063882
PCT Pub. Date: Apr. 4, 2019

(65) Prior Publication Data
US 2021/0401365 A1   Dec. 30, 2021

(30) Foreign Application Priority Data

Sep. 28, 2017 (FI) ..................................... 20175862

(51) Int. Cl.
*A61B 5/00* (2006.01)
*A61B 5/117* (2016.01)
(Continued)

(52) U.S. Cl.
CPC .......... *A61B 5/4824* (2013.01); *A61B 5/0205* (2013.01); *A61B 5/117* (2013.01);
(Continued)

(58) Field of Classification Search
CPC ... A61B 5/4824; A61B 5/0205; A61B 5/7246; A61B 5/02405; A61B 5/0816;
(Continued)

(56) References Cited

U.S. PATENT DOCUMENTS

| 8,475,367 B1 * | 7/2013 | Yuen | A61B 5/02007 600/300 |
| 2003/0163710 A1 * | 8/2003 | Ortiz | H04L 63/0861 713/186 |

(Continued)

FOREIGN PATENT DOCUMENTS

| CN | 105556529 | 5/2016 | |
| KR | 10-1689021 | 12/2016 | |
| WO | 01/16938 | 3/2001 | |
| WO | WO2016124482 A1 * | 11/2016 | ............. G06F 19/00 |

OTHER PUBLICATIONS

S. Sowmyasudhan, et al., "A Wireless Based Real-Time Patient Monitoring System", International Journal of Scientific & Engineering Research, vol. 2, Issue 11, Nov. 2011, 7 pages.
(Continued)

*Primary Examiner* — Nathan J Jenness
(74) *Attorney, Agent, or Firm* — Nixon & Vanderhye PC

(57) ABSTRACT

There is provided a system for determining a sound source and a method thereof. The system comprises: an audio sensor; a biosensor for measuring one or more biosignals of a subject; and a processing unit communicatively coupled with the audio sensor and the biosensor, the processing unit configured to perform operations comprising: obtaining audio data from the audio sensor and biosignal data from the biosensor, the audio data and the biosignal data being time-synced with each other, detecting, based on the audio data, a sound exceeding a threshold, and determining that the sound exceeding the threshold originates from the subject if the biosignal data indicates a change in the one or more biosignals at a corresponding time.

20 Claims, 8 Drawing Sheets

(51) Int. Cl.
- *A61B 5/024* (2006.01)
- *A61B 5/08* (2006.01)
- *G16H 40/67* (2018.01)
- *G16H 50/30* (2018.01)
- *G16H 50/70* (2018.01)
- *A61B 5/0205* (2006.01)
- *A61B 7/04* (2006.01)
- *G08B 21/02* (2006.01)
- *G10L 25/66* (2013.01)
- *H04R 1/04* (2006.01)
- *H04R 1/08* (2006.01)

(52) U.S. Cl.
CPC .............. *A61B 5/7246* (2013.01); *A61B 7/04* (2013.01); *G08B 21/0225* (2013.01); *G10L 25/66* (2013.01); *G16H 40/67* (2018.01); *G16H 50/30* (2018.01); *G16H 50/70* (2018.01); *H04R 1/04* (2013.01); *H04R 1/08* (2013.01); *A61B 5/02405* (2013.01); *A61B 5/0816* (2013.01)

(58) Field of Classification Search
CPC ....... A61B 5/117; A61B 5/4803; A61B 5/002; A61B 5/7275; A61B 5/7282; A61B 5/746; G16H 40/67; G16H 50/30; G16H 50/70; G10L 25/66
USPC .................................................. 600/300, 301
See application file for complete search history.

(56) References Cited

U.S. PATENT DOCUMENTS

| | | |
|---|---|---|
| 2005/0187437 A1 | 8/2005 | Matsugu et al. |
| 2008/0139907 A1* | 6/2008 | Rao ..................... A61B 5/1171 600/323 |
| 2009/0124863 A1 | 5/2009 | Liu et al. |
| 2011/0087079 A1 | 4/2011 | Aarts |
| 2014/0085050 A1* | 3/2014 | Luna ..................... G07C 9/37 340/5.82 |
| 2014/0276549 A1 | 9/2014 | Osorio |
| 2014/0278388 A1 | 9/2014 | Watson et al. |
| 2016/0080550 A1 | 3/2016 | Kwon et al. |
| 2016/0217260 A1 | 7/2016 | Aarts et al. |
| 2016/0378964 A1* | 12/2016 | Singh ..................... G06F 21/32 340/5.52 |
| 2017/0041699 A1 | 2/2017 | Mackellar et al. |

OTHER PUBLICATIONS

Search Report of Finnish Patent Application No. 20175862 dated Mar. 2, 2018, 2 pages.
International Search Report for PCT/FI2018/050693 dated Jan. 2, 2019, 2 pages.
Written Opinion of the ISA for PCT/FI2018/050693 dated Jan. 2, 2019, 5 pages.
International Preliminary Report on Patentability for PCT/FI2018/050693 dated Aug. 27, 2019, 6 pages.

* cited by examiner

SYSTEM FOR DETERMINING SOUND SOURCE

This application is the U.S. national phase of International Application No. PCT/FI2018/050693 filed Sep. 26, 2018 which designated the U.S. and claims priority to FI Patent Application No. 20175862 filed Sep. 28, 2017, the entire contents of each of which are hereby incorporated by reference.

FIELD

The present invention relates to determining sound source. More particularly, the present invention relates to determining a subject that generates sound.

BACKGROUND

Audio sensors can be used to measure sound from a plurality of subjects. It may be beneficial for different systems to identify the subject that is generating sound. One example of such system may be a system that is used to measure generated sound by a plurality of patients. If sound input is detected from the plurality of patients, it may be beneficial to further identify the patient that generates the sound. Such identifying may be useful for other types of systems as well.

BRIEF DESCRIPTION

There is provided a system for determining a sound source, the system comprising: an audio sensor; a biosensor for measuring one or more biosignals of a subject; and a processing unit communicatively coupled with the audio sensor and the biosensor, the processing unit configured to perform operations comprising: obtaining audio data from the audio sensor and biosignal data from the biosensor, the audio data and the biosignal data being time-synced with each other, detecting, based on the audio data, a sound exceeding a threshold, and determining that the sound exceeding the threshold originates from the subject if the biosignal data indicates a change in the one or more biosignals at a corresponding time. Some embodiments are disclosed in dependent claims.

One or more examples of implementations are set forth in more detail in the accompanying drawings and the description below. Other features will be apparent from the description and drawings, and from the claims.

BRIEF DESCRIPTION OF THE DRAWINGS

In the following embodiments will be described in greater detail with reference to the attached drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
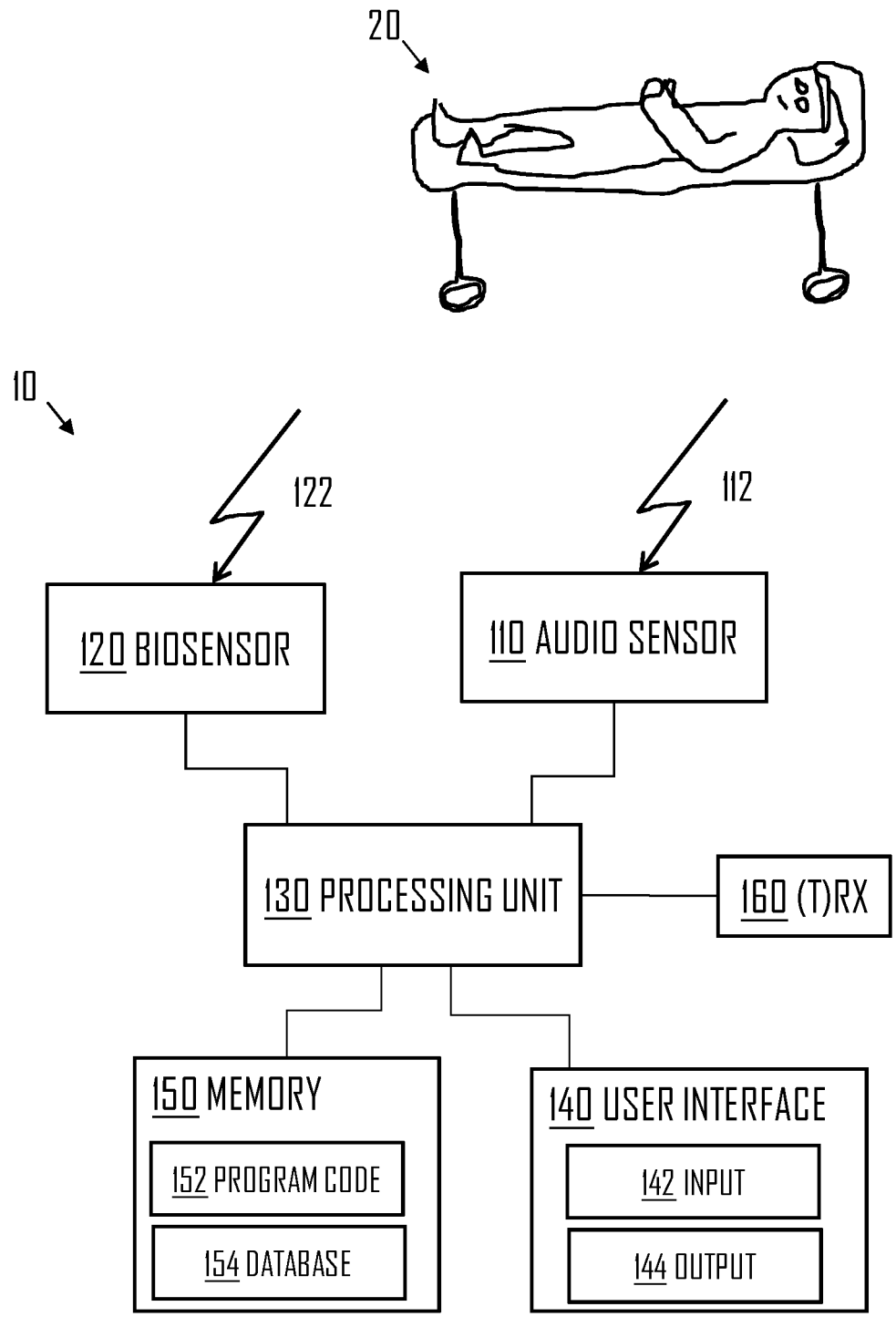
FIG. 1 illustrates a system according to an embodiment.

FIG. 1 illustrates a system 10 for determining a sound source, wherein the system comprises an audio sensor 110. The audio sensor may be any kind of audio sensor, such as a microphone, configured to convert sound into an electrical signal. That is, the audio sensor 110 may convert an audio input 112 into an audio signal (i.e. electrical audio signal). The audio sensor 110 may comprise one or more audio transducers. For example, to measure intensity of sound, it may be beneficial to use more than one microphone. Example of an audio signal 410 may be seen in FIG. 4A.

The system 10 comprises a biosensor 120 for measuring one or more biosignals of a subject 20. The subject may refer to, for example, a person or a human. For example, the subject may be a patient, such as a patient in a hospital. The biosensor 120 may have a measurement head or heads configured to be placed in contact with a body tissue of the subject. The biosensor 120 may be configured to measure one or more biosignals 122 of the subject. Biosignals may comprise, but are not necessarily limited to, Heart Rate Variability (HRV), heart rate, respiration rate, blood oxygen level, temperature, and blood pressure. Measuring such biosignals is generally known from the art of biosignal measuring, but not applied in the present field. The biosensor 120 may nonetheless measure said biosignals 122 and provide raw measurement data and/or processed measurement data as an output. For example, the biosensor 120 may pre-process the raw measurement data and provide pre-processed measurement data as an output. Pre-processing may comprise, for example, filtering, modulating, demodulating and/or converting (e.g. analog-to-digital converting) the detected biosignal or biosignals before outputting the pre-processed biosignal data. However, in some embodiments, the processing unit 130 receives real-time audio data and biosignal data from the respective sensors, and process the data in real-time as described below. Naturally, there may be some delay caused by, for example, non-ideal transmission link(s). Biosensor 120 may comprise one or more sensors, such as optical heart activity sensor, electrode(s) (i.e. electrode based measurements of heart rate and/or respiration rate), temperature sensor, blood pressure sensor, blood oxygen level sensor. Hence, one or more biosignals of a subject may be measured. As described such sensors are generally known in the art of measuring biosignals and will not be disclosed in further detail. But as also described, using such sensors in the proposed solution is not known.

The system 10 further comprises a processing unit 130. The processing unit 130 may comprise one or more processors coupled with one or more memories 150 of the system 110, the one or more memories 150 comprising program code 152, wherein the program code 152 may cause the one or more processors to execute functions of the processing unit 130. In another example, the processing unit 130 comprises one or more circuitries configured to perform the functions of the processing unit 130. In another example, the processing unit 130 comprises both processor(s) controlled at least partially by the program code, and dedicated circuitry or circuitries executing a preconfigured functionality. Such dedicated circuitries may include, for example, Field-Programmable Gate Array (FPGA) and/or Application Specific Integrated Circuitry (ASIC) circuitries.

The processing unit 130 may be communicatively coupled with the audio sensor 110 and the biosensor 120. Said coupling may be established using wired and/or wireless communication. For the communication, the processing unit 130 may utilize a communication circuitry 160 (shown as (T)RX 160 in FIG. 1). The communication may be one-directional (e.g. receiving data from the sensors by the processing unit 160) or bidirectional (e.g. receiving data from sensor and possibly configuring the sensors). TRX 160 may not be necessary if the sensors 110, 120 are connected to the processing unit via conductive traces (e.g. wires). However, TRX 160 may utilized to enable use of one or more communication protocols and/or interfaces, such as Local Area Network (LAN), Universal Serial Bus (USB), Bluetooth (e.g. Bluetooth smart), Wireless LAN (WLAN), infrared, and/or cellular communication (e.g. 2G, 3G, 4G, 5G). For example, the TRX 160 may enable communication on industrial, scientific and medical (ISM) radio bands according to one or more communication protocols.

The processing unit 130 may be configured to obtain audio data from the audio sensor 110 and biosignal data from the biosensor 120. The audio data may carry and/or comprise information about the detected audio signal and the biosignal data may carry and/or comprise information about the detected biosignal(s). The audio data and/or biosignal data may be received directly from the respective sensors 110, 120 or it may be stored (e.g. by the respective sensor) to the memory 150 (e.g. in a database 154 of the memory 150), wherein the processing unit 150 may obtain (e.g. fetch) the data from the memory 150.

The audio data and the biosignal data may be time-synced (i.e. time-synchronized) with each other. This may mean that the audio data and the biosignal data represent measurements from the same measurement period and different samples in the audio data timely correspond to different samples in the biosignal data. For example, if a first audio sample is measured at a first time instant, the biosignal data may comprise a first biosignal sample measured at said first time instant. Hence, the first audio sample may timely correspond to the first biosignal sample. Similarly, for example, if a second audio sample is measured at a second time instant (e.g. being different than the first time instant), the biosignal data may comprise a second biosignal sample measured at said second time instant. Hence, the second audio sample may timely correspond to the second biosignal sample. It needs to be understood that there may be a plurality of different samples over a certain time period, for example. So, the measurement of sound may be performed simultaneously with the measurement of the biosignals(s). It needs to be noted that even though the measurement would be simultaneous, in some cases, it may be possible that the audio data and the biosignal data is not time-synced due to, for example, delay in the system. Hence, the system 10 (e.g. processing unit) may sync (i.e. synchronize) the audio data and the biosignal data if they are not initially in-sync. It is further noted that the time-synced audio data and biosignal data should be understood broadly to cover situations in which a certain event (e.g. measuring period or periods) at a certain time instant(s) (e.g. time period or periods) may be detected from both the audio data and the biosignal data. For example, measuring period may be 2-30 seconds, and audio signal and biosignal may be measured simultaneously with the accuracy of 1-1000 milliseconds. That is, the different signals may be measured for said measuring period, and their correspondence with each other may be within said accuracy limit.

The processing unit 130 may be configured to detect, based on the audio data, a sound exceeding a threshold. That is, the audio sensor 110 may measure sound, wherein a measured sound exceeds the threshold. This may be detected by the processing unit. The detection may simply mean that the processing unit 130 initiates some further action if the threshold is exceeded. In one example, exceeding the threshold may mean that the sound is equal to or over a certain threshold. Moreover, in some embodiments, the threshold refers to sound pressure threshold (e.g. decibel (dB)), i.e. if sound pressure (dB) exceeds a certain threshold, the processing unit 130 may initiate the further action. Another example may be use of measured sound intensity and corresponding sound intensity threshold. In some examples, said threshold may be for some other characteristic of sound. For example, a pitch, loudness, amplitude or duration of measured sound may be compared against respective threshold. For example, if pitch is equal to or over certain threshold, the further action may be initiated. The described threshold to determine whether the sound exceeds the threshold or not, may be substantially a non-zero threshold (e.g. over 0 dB or over a certain defined dB level). Also, it may be possible to utilize more than one threshold or the threshold may require more than one characteristics of sound to exceed a certain limit, e.g. pitch and sound pressure may both need to be over certain thresholds. Also, in some embodiments, the processing unit 130 may utilize speech-recognition software (e.g. stored in the memory 150) and/or hardware to determine if the detected sound is generated by a speech organ and/or is human voice. That is, such speech-recognition may be used to detect sounds generated by humans instead of generally all sound which exceed the threshold (e.g. air conditioning, footsteps, metallic sounds etc.). The different thresholds and sound characteristics may thus be used in various ways to configure the system 10 to detect sounds of interest.

The processing unit 130 may further be configured to determine that the sound exceeding the threshold originates from the subject 20 if the biosignal data indicates a change in the one or more biosignals at a corresponding time. Corresponding time may refer to the time period and/or time instant when the sound exceeding the threshold is measured by the audio sensor 110. However, the detecting the sound, by the processing unit 130 from the audio data, may happen with a certain delay due to delay in measuring and/or processing. Hence, the system 10 may be used to determine and/or verify that the sound exceeding the threshold (measured by the audio sensor 110) originates and/or is generated by the subject 20. There may be a plurality of different reasons to perform such verification. One may be that if both the audio sensor 110 and the biosensor 120 measure only the same subject 20, the biosensor 120 may be used to verify that the detected sound (detected sound may refer to the sound exceeding the threshold) originates from the subject 20 instead of from the environment, for example. Also, the determining the sound source may be beneficial as the sound may originate from another subject (e.g. person) nearby (e.g. another patient in the adjacent bed). Another example may be shown in FIG. 2: audio sensor 110 may be configured to measure sound such that it may detect sounds from a plurality of subjects. Different biosensors 120A-D each associated with a certain subject of the plurality of subjects (e.g. configured to measure biosignal(s) of a certain subject). The processing unit 130 may thus determine which of the subjects if any generates or generated detected sound based on detecting changes in the biosignal data from the different biosensors 120A-D. In an embodiment, the system comprises only one audio sensor 110. Said only one audio sensor 110 may be configured to measure sound from a plurality of subjects (e.g. room audio sensor), and the biosensor(s) 120 may be used to determine which of the subjects generates sound.

In an embodiment, system 10 comprises a user interface 140. The user interface 140 may comprise an input user interface 142 and/or output user interface 144. The input 142 may comprise keyboard, virtual keys, voice control circuitry and the like. The input 142 may be used to control the operation of the processing unit 130 and/or the sensors 110, 120. For example, the input 142 may be used to switch sensors 120 on/off. The output 144 may comprise a display element(s) (e.g. display and/or indication lights) and/or a speaker.

The processing unit 130 may output an indication indicating and/or identifying a subject, wherein the indication is outputted if the sound exceeding the threshold is determined to originate from said subject. Outputting may comprise outputting the indication via the output user interface 144, storing the indication to the database 154 and/or transmitting the indication to an external device via the TRX 160. For example, if the indication is transmitted to the user interface 140 communicatively coupled with the processing unit (wired and/or wireless connection), the user interface 140 may receive the indication and output the indication. Outputting may comprise displaying the indication or associated information and/or audibly outputting the indication or associated information. Hence, the system 10 may be used to indicate the subject generating the sound. This may be valuable information in hospital environment for example.

Figure 2:
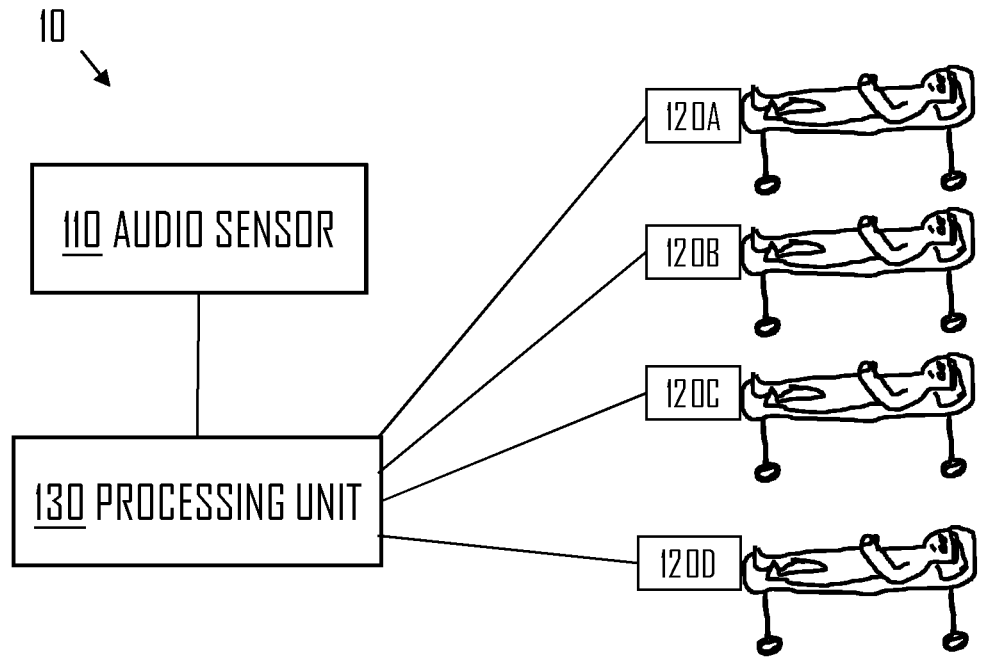
FIG. 2 illustrates an embodiment.

Referring to the embodiment of FIG. 2, as described the system may comprise a plurality of biosensors 120A, 120B, 120C, 120D associated with a plurality of subjects, wherein the processing unit 130 is configured to identify a subject generating sound based on the acquired biosignal data from the plurality of biosensors 120A, 120B, 120C, 120D. E.g. one biosensor may be associated with one subject. In an embodiment, the processing unit 130 is configured to determine that the subject generating sound is the subject associated with the highest or largest change in the biosignal at the corresponding time (i.e. the time corresponding to the generation of the sound). For example, if there are two subjects and heart rate of both subjects increases during the corresponding time. However, one subject's heart rate increases 10% and the other subject's heart rate increases 5%. Thus, the processing unit may determine that the subject with more increase in heart rate is the subject generating the sound. It is noted that such determination may not always be totally accurate. However, the accuracy may suffice for many different implementations. It is also possible that the system 10 does not determine the sound source for all sounds exceeding the threshold. However, the accuracy may suffice for many different implementations.

In an embodiment, the system 10 (e.g. system of FIG. 1 and/or 2) comprises a measuring device having a body, the body at least partially enclosing the audio sensor 110 and the biosensor 120. That is, the audio sensor 110 and the biosensor 120 may be arranged in a same measuring device configured to be attached to the subject. The measuring device or devices may be communicatively coupled with the processing unit 130. In an embodiment, the processing unit 130 is comprised in the measuring device. The measuring device may further comprise a strap or similar attachment means to enable attachment of the measuring device to the subject such that the different sensors may perform measurements accordingly.

In an embodiment, the system 10 comprises a plurality of audio sensors 110. Each audio sensor 110 may be associated with a certain subject similarly as the biosensors 120A-D. For example, the audio sensor 110 may be configured to be placed on a chest of a subject to measure sound originating from the speech organs of the subject (i.e. sounds via mouth).

In an embodiment, the system 10 comprises a server computer or server computers configured to obtain stored audio and/or biosignal data from the database 154. The server computer may comprise the processing unit 130 and/or its functionalities. Hence, it may be possible to use, for example, sensors to measure at a certain location and store the data to the database 154, and perform needed calculations at another location distinct from the measuring location. This may enable remote monitoring of the subjects, for example.

Figure 3:
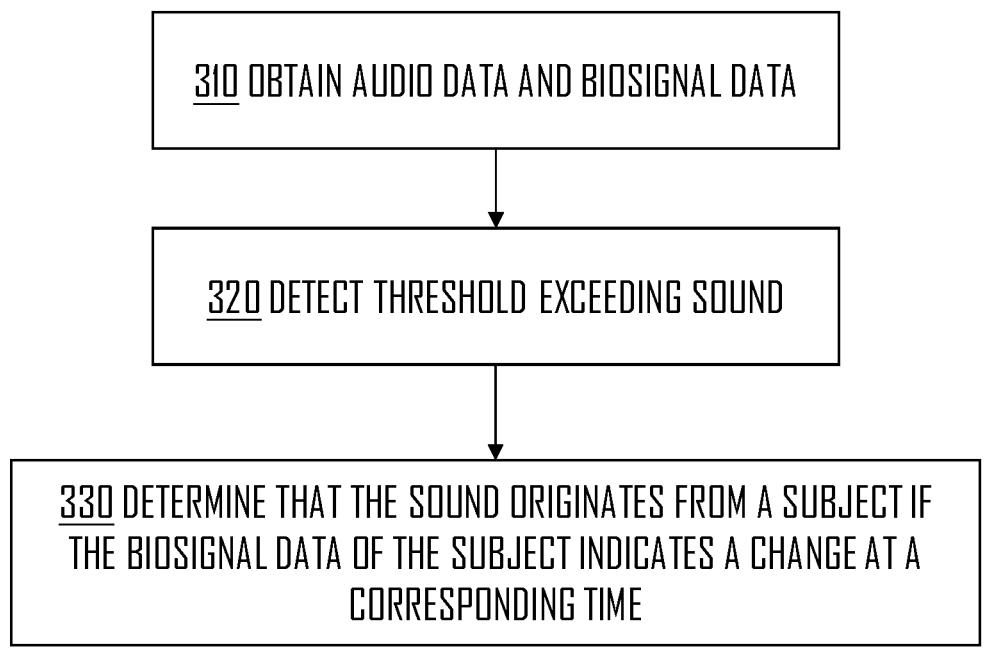
FIG. 3 illustrates a flow diagram according to an embodiment.

FIG. 3 shows a flow diagram of a method for determining a sound source according to an embodiment. Referring to FIG. 3, the method comprises: obtaining 310, by a processing unit, audio data from an audio sensor and biosignal data from a biosensor for measuring one or more biosignals of a subject, the audio data and the biosignal data being time-synced with each other; detecting 320, based on the audio data, a sound exceeding a threshold; and determining 330 that the sound exceeding the threshold originates from the subject if the biosignal data indicates a change in the biosignal at a corresponding time.

Figure 4A:
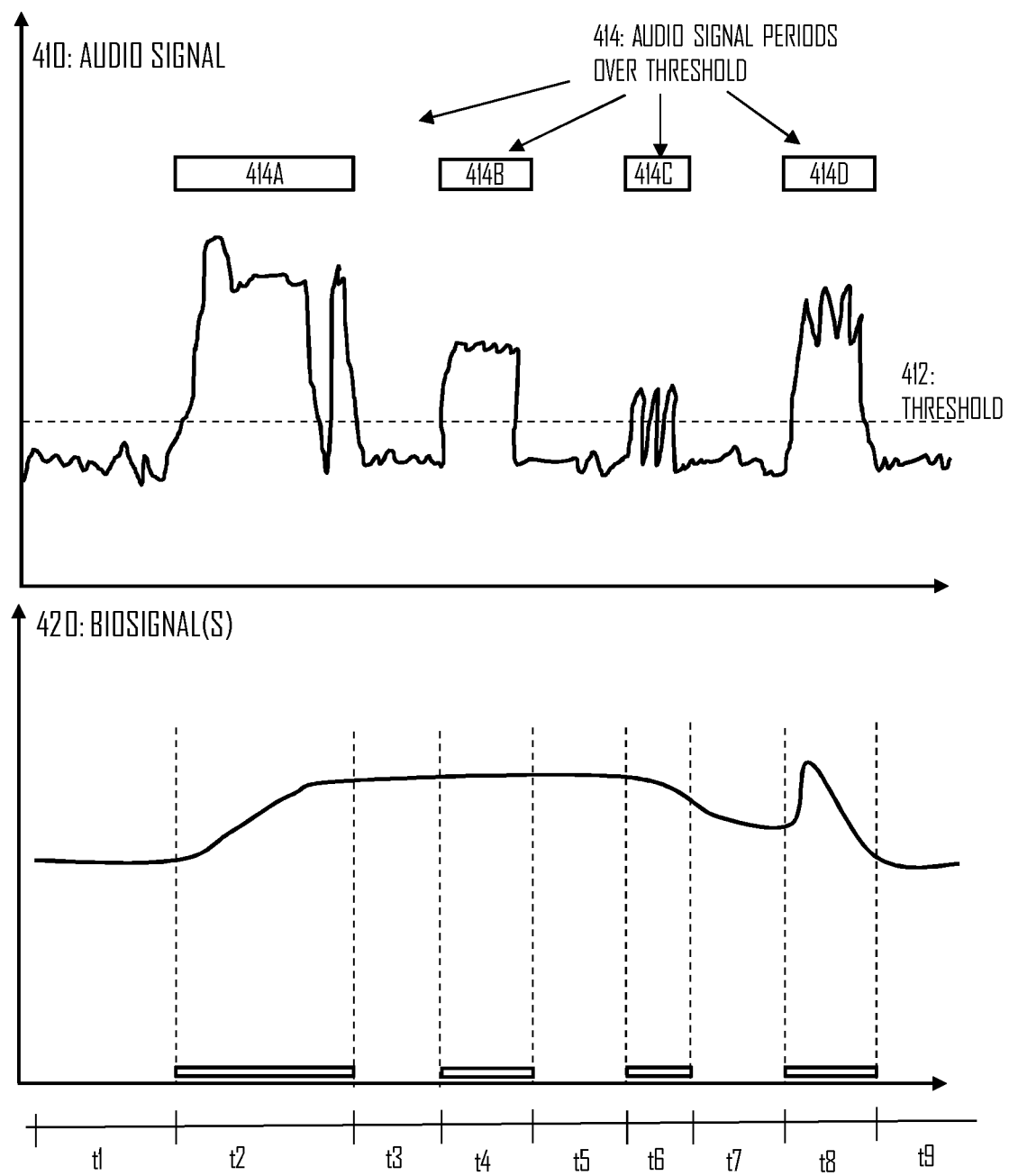
FIGS. 4A, 4B, 4C, and 4D illustrate some embodiments.

Let us now look closer on some embodiments of FIGS. 4A, 4B, 4C, and 4D. Referring to FIG. 4, audio signal 410 measured by the audio sensor 110 and biosignal 420 measured by the biosensor 120 are shown. Both signals may be indicated over a measurement period comprising sub-periods t1-t9 and are time-synced with each other as described earlier. The processing unit 130 may detect, from the audio data, that the audio signal 410 exceeds a threshold 412 during periods 414A-D (i.e. periods 414). The audio signal 410 may indicate, for example, measured sound pressure, but may also indicate some other characteristic of sound as described earlier. It is pointed out that distance from the sound source affects the measured sound intensity. Said periods 414A-D correspond to time periods t2, t4, t6, and t8 of the biosignal data. I.e. period 414A may correspond to t2, period 414B may correspond to t4, period 414C may correspond to t6, and period 414D may correspond to t8, as shown in FIG. 4A. The processing unit 130 may detect that the biosignal data indicates a change or changes in the biosignal 420 during periods t2, t6, and t8. I.e. during period t2, the biosignal rises, during period t6, biosignal declines and during period t8 the biosignal both rises and declines. Hence, there may be a detected change in the biosignal during the periods t2, t6, t8 associated with the sound exceeding the threshold 412. However, during period t4, the biosignal does not indicate change. Hence, it may be determined that the sound during period 414B may originate from some other source than the subject associated with the biosignal 420. Moreover, the processing unit 130 may examine the biosignal data over a longer period compared with the period associated with the generation of sound. For example, the period t2 may longer from both ends compared with period 414A. Thus, the processing unit 130 may use biosignal data from the period when the sound is generated and also from time before and/or after the sound is generated. For example, this may reveal a deep breath before sound is generated.

In an embodiment, the system 10 (e.g. processing unit 130) utilizes a plurality of sound thresholds. E.g. one may be the threshold 412 (e.g. for sound intensity) and another may be for some other sound characteristics, such as sound pitch.

In an embodiment, all thresholds need to be exceeded before the system 10 initiates the determining the sound source based on the biosignal(s). In an embodiment, at least one of said thresholds need to be exceeded before the system 10 initiates the determining the sound source based on the biosignal(s).

It is pointed out that audio signal threshold(s) may be automatic. I.e. the system 10 may be configured to adapt to detected noise and/or background sound level. For example the system 10 (e.g. processing unit 130) measures long term sound average for example 1 minute and sets the threshold to be 50%-100% more than the long term background average sound level. Hence, in an embodiment, the system 10 is configured to be initialize the sound source measurement by first detecting sound (e.g. background noise) for a certain time period, and adjusting the threshold(s) based on the detected sound. After the thresholds are adjusted, the system 10 may initiate the actual sound source determination based on the biosignals and the sounds exceeding said threshold(s).

It is noted that the change may be detected using plurality of different criteria. One may be to utilize a certain threshold which defines that the change needs to be of certain volume to trigger the processing unit 130 to determine that the subject generates the sound. For example, heart rate needs to increase a certain percent, HRV needs to decrease a certain percent and/or a rolling average of respiration rate needs to decrease a certain percent. These are just few examples of detecting the change in the biosignal data.

Figure 4B:
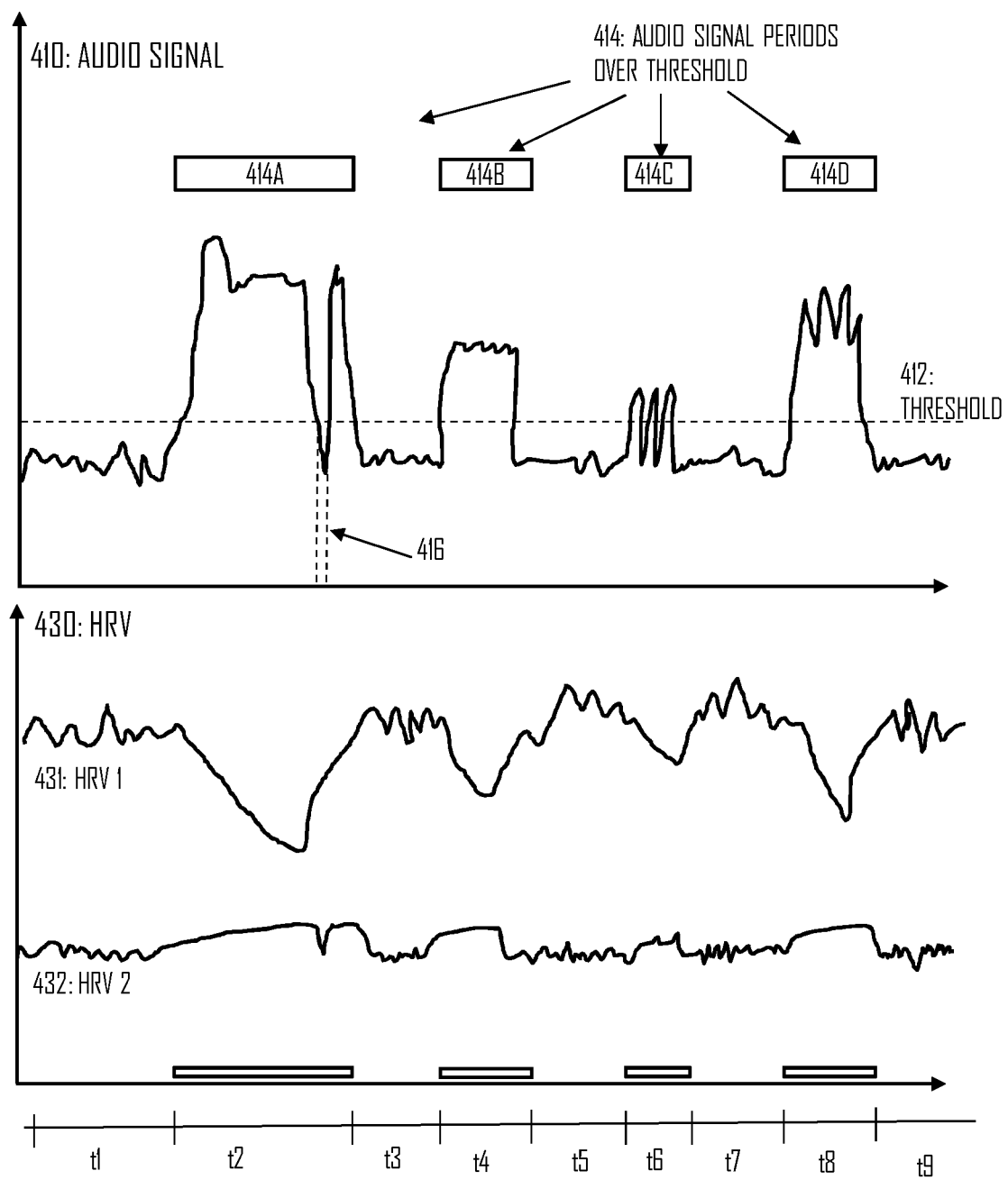

Referring now to FIG. 4B, the same audio signal 410 may be shown as in FIG. 4A. It is further noted that during period 414A, the sound level or sound pressure decreases below the threshold 412 for period 416. This may not necessarily affect the sound source determination as the period 416 may be shorter than a certain time threshold. Hence, for example, the determination about the sound source based on the biosignal data may be performed for the whole period 414A. However, for period 414B, the determination may be independent as the time between periods 414A and 414B may be equal to or over said time threshold. This may mean time between detected sounds over the threshold 412.

In the examples of FIG. 4B, the biosignal 420 may be or comprise HRV 430. HRV may change during audio signal generated by a subject (e.g. person). According to a first example, first HRV 431 (i.e. HRV 1) associated with a first subject is shown. HRV (i.e. time between successive heart beats) may behave differently with different subjects when the subject is generating sound. For example, if the first person generates sound during periods 414, his/her HRV may decrease during the respective or corresponding time periods t2, t4, t6, t8. As shown in FIG. 4B, HRV1 431 decreases during all periods t2, t4, t6, t8. Hence, there is a change in the biosignal, and thus the processing unit 130 may determine that the sound source is the first person.

According to a second example of FIG. 4B (i.e. independent from the first example), a second HRV 432 (i.e. HRV 2) associated with a second subject is shown. For example, if the second person generates sound during periods 414, his/her HRV may increase or elevate during the respective or corresponding time periods t2, t4, t6, t8. Although, the difference or change in the HRV 2 may be quite small, the processing unit 130 may still determine that the second subject generates the sound.

According to a third example of FIG. 4B, the HRV 430 may be measured from more than one subject simultaneously to determine who generates sound. Hence, for example, it may be determined, by the processing unit 130, that the sound is generated by the first subject associated with HRV 1, because change in the HRV 1 is greater during each period t2, t4, t6, t8 than the change in HRV 2 associated with the second subject. For example, if the change in HRV 2 would be greater during period t4, the processing unit 130 may then determine that the sound during periods 414A, C, D is generated by the first subject and the sound during period 414B is generated by the second subject. In other words, the HRV 430 may correlate with the audio signal 410, and the processing unit 130 may determine based on the correlation which subject generates sound.

Figure 4C:

Referring to FIG. 4C, the biosignal 420 may be or comprise breathing 440. Breathing frequency or respiration rate may change during output of sound by a subject. In the example, breathing may be indicated as breathing pulses; one pulse in the graph may denote one breathe (i.e. inhale and exhale) by the subject. As shown in the Figure, the subject does breathe or breathes with a greater interval during each period t2, t4, t6, t8. Hence, the processing unit 130 may determine that the subject generates the sound as he/she may not (at least) substantially breathe during output of voice. Breathing may be detected using, for example, chest-mounted electrodes. Although not shown in FIG. 4C, respiration rate may be one measurable parameter which may be used to determine whether the breathing of the subject changes during the periods t2, t4, t6, t8. That is, if the subject does not breathe, his/her respiration rate may decrease (i.e. average over a certain time period). For example, it may be possible to measure breathing pattern and/or breathing frequency as a rolling average, for example, every 2 seconds over 10 seconds to determine the possible change, and thus the source of the sound output.

Figure 4D:
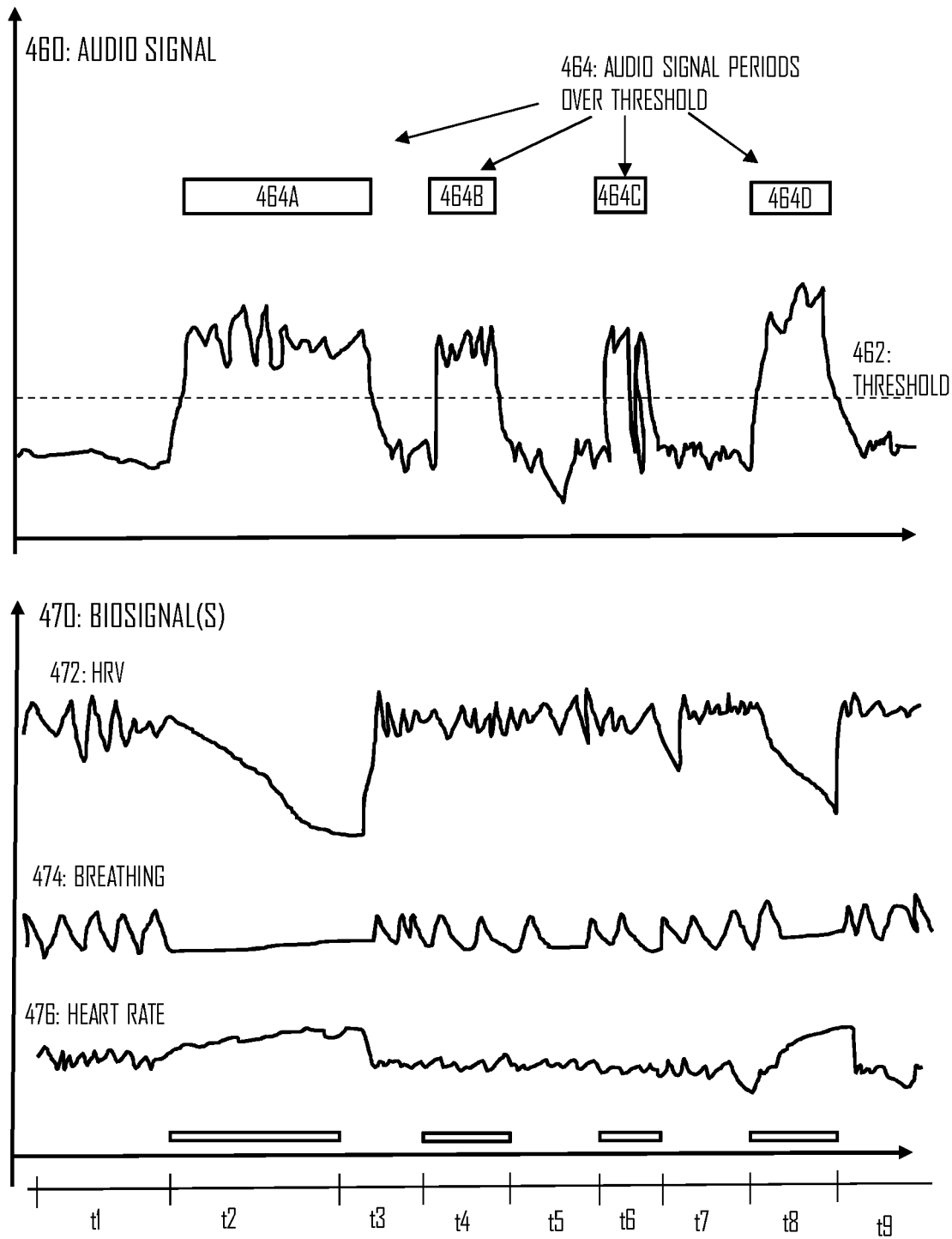

It is possible to use other biosignals additionally or alternatively to determine the audio source. For example, heart rate may provide one suitable biosignal indicator. In other words, the biosignal data provided by the biosensor 120 or biosensors (e.g. 120A-D) may comprise heart rate data, heart rate variation data, and/or respiration rate data. Referring now to FIG. 4D, an audio signal 460 and biosignals 470 are shown. Biosignals 470 may comprise HRV 472, breathing 474, and/or heart rate 476, to name a few examples. Similarly, as in FIGS. 4A to 4C, the audio signal 460 may exceed a threshold 462 during periods 464 comprising periods 464A-D. These periods may correspond to periods t2, t4, t6, t8. In the example of FIG. 4D, all biosignals may be measured from the same subject. For example, HRV 472, breathing 474 and/or heart rate 476 may be measured as a rolling average, for example, every 2 seconds over 10 seconds. Some other type of averaging or determination may be equally possible. It is possible to compare the biosignals to measured audio signal 460 which is exceeding the audio threshold 462. In FIG. 4D, the correlation can be seen in the periods t2 and t8. So, the system 10 may define that the sound is generated by the subject. During the periods t4 and t6 there is no correlation between biosignal and audio signal, so the audio signal is determined, by the processing unit 130, to originate from another subject or source. In an embodiment, the processing unit 130 outputs an indication that the sound originates from some other subject based on the determination.

Different biosignals may be used in multiple different ways. One is that if even one indicates a change or substantial change, the processing unit 130 may determine that the sound source is the subject. According to an embodiment, the processing unit 130 is configured determine that the sound exceeding the threshold (e.g. 462) originates from the subject only if the biosignal data indicates a change at the corresponding time in at least two of the following biosignals: heart rate, heart rate variation, respiration rate. In an embodiment, the requirement may be a detected change in each of said biosignals, i.e. heart rate 476, heart rate variation 472, and respiration rate (or in more general terms: breathing 474).

Based on the determination by the processing unit 130, the processing unit 130 may cause output of a notification or an indication which identifies the subject as discussed above. For example, indication may be stored in the audio data so that it indicates which subject has generated sound. For example, the indication may be outputted in real-time so that caretakers may know which patient is producing sound and act accordingly (e.g. remote controlling of a plurality of subjects).

Figure 5A:
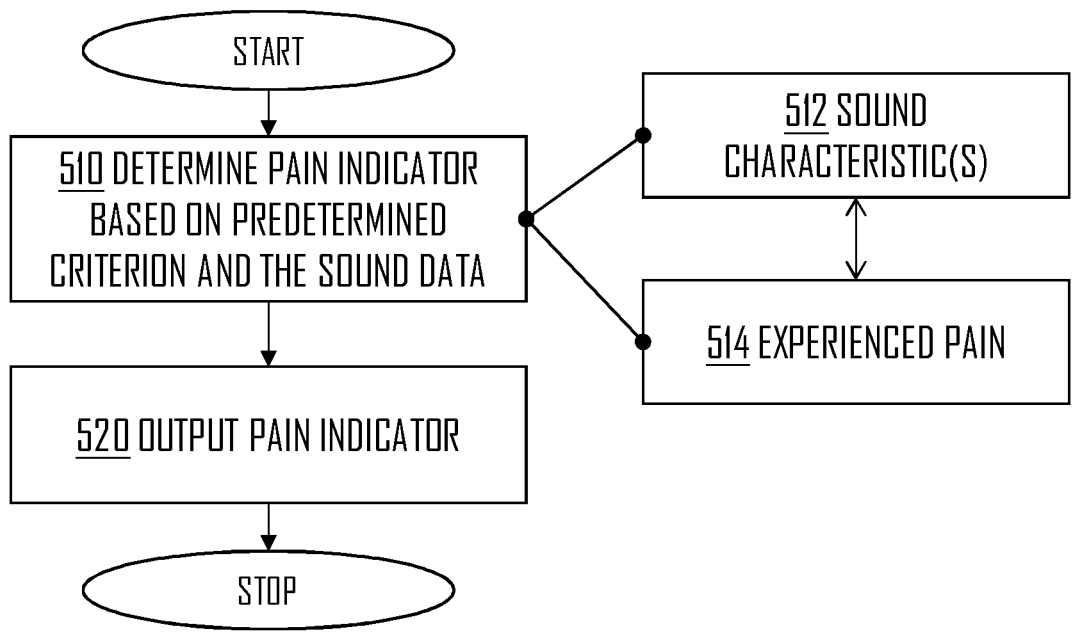
FIG. 5A illustrates a flow diagram according to an embodiment.

The system 10 of FIGS. 1 and/or 2 may further be for measuring subject experienced pain. FIG. 5A illustrates an embodiment of such configuration. Referring to FIG. 5A, the processing unit 130 may be configured to determine 510, based on at least one predetermined criterion and the sound exceeding the threshold, a pain indicator for indicating experienced pain by the subject. The system 10 may further output 520 the pain indicator. Outputting the pain indicator may comprise similar outputting means and/or ways as outputting the indicator identifying the subject (e.g. output via user interface, storing to database, transmitting to external device).

In an embodiment, the pain indicator is determined based on a predetermined correlation between at least one characteristic of sound 512 and subject experienced pain 514. The characteristics of sound were discussed previously. One example of such characteristic may be sound pressure or sound level (see example of FIG. 5C) and another may be pitch of sound (see example of FIG. 5D).

Figure 5B:
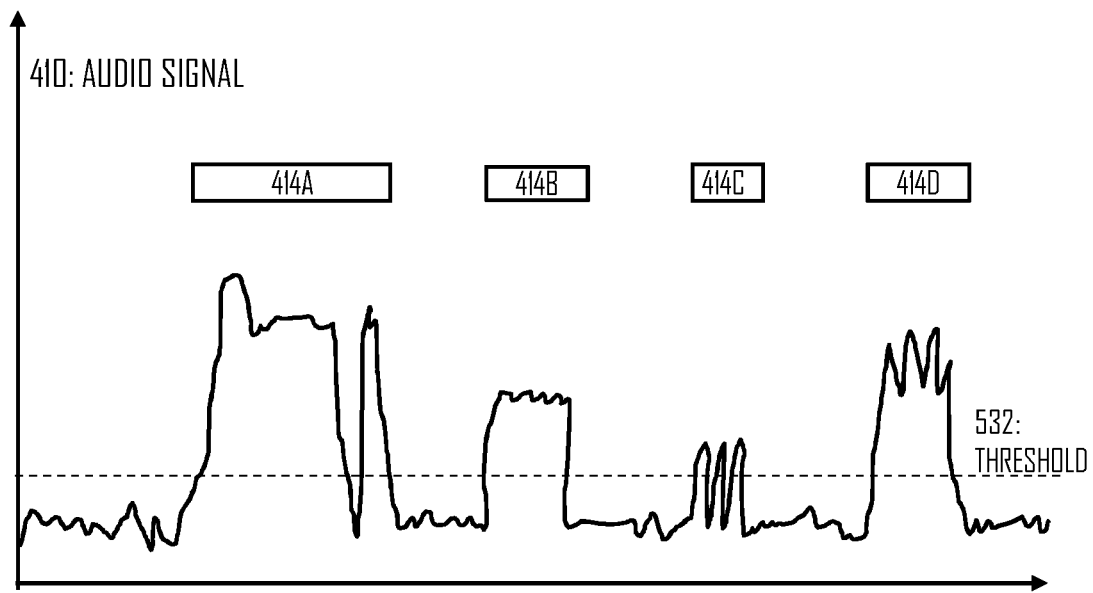
FIGS. 5B, 5C, and 5D illustrate some embodiments.
Figure 5C:
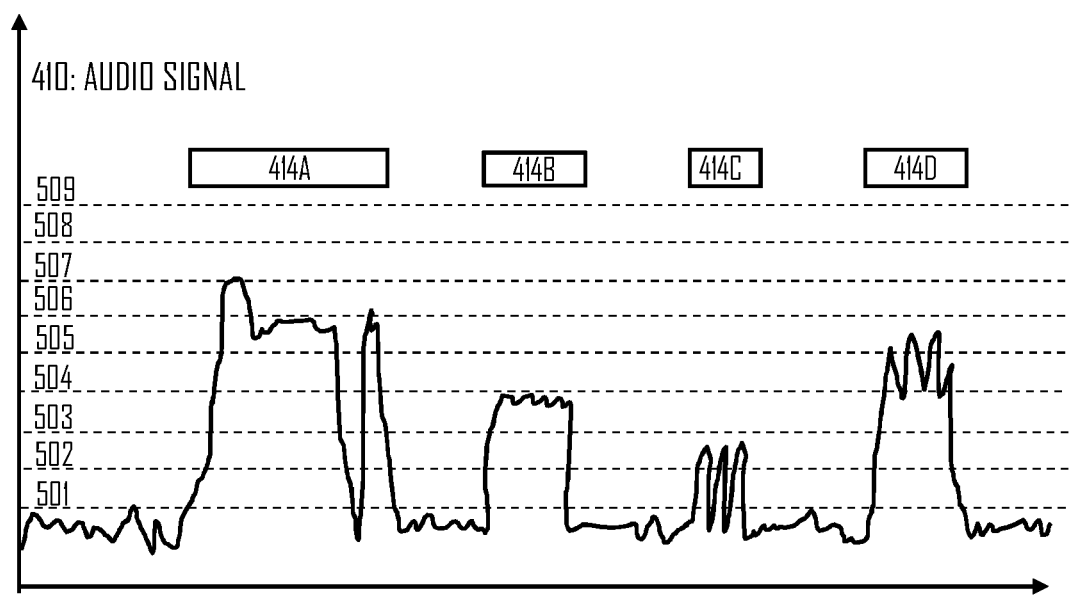

Referring to FIG. 5B, the audio signal 510 may represent sound pressure (or the graph represent sound pressure of the signal). The pain indicator may be determined based on a predetermined correlation between measured sound pressure and the subject experienced pain. For example, a threshold 532 may represent a threshold for generated sound for which the source may be determined. Additionally, the same threshold 532 may indicate a sound pressure level that is preconfigured to be indicative of pain. That is, if the subject is determined to generate said sound, the processing unit 130 may further determine that the sound exceeding the threshold 532 indicates that the subject is experiencing pain.

Additionally or alternatively, the processing unit 130 may apply other thresholds which each may indicate different levels of experienced pain. One example of this may be seen in FIG. 5C, wherein a plurality of thresholds 501-509 are used, each threshold being associated with a different level of experienced pain. For example, sound pressure between thresholds 501 and 502 may indicate level 1 pain, whereas sound pressure between thresholds 507 and 508 may indicate level 7 pain, and so on. There are multiple ways to preconfigure certain pain levels with audio output.

Figure 5D:
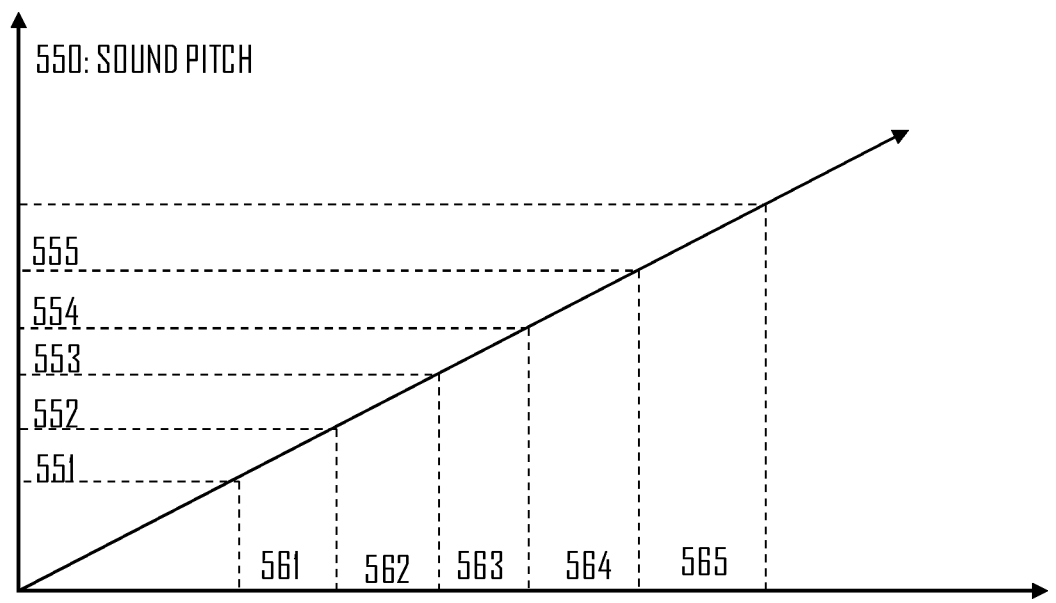

Another example of sound characteristics being associated with certain level of pain may be shown in FIG. 5D representing pitch of sound 550 with respect to pain indicator 560. In this example, there may be different levels of experienced pain 561-565 indicated with the indicator 560. Now, the pitch thresholds 551-555 or more precisely sound pitch between subsequent thresholds may be preconfigured to correspond to a certain pain level. For example, sound pitch between thresholds 551-552 may correspond to experienced pain level 561. It may be possible to use multiple different characteristics of sound (e.g. pitch and sound pressure) to generate a more accurate correspondence between sound and experienced pain by a subject or subjects. For example, audio recognition may be utilized which may be configured to determine from the sound whether the produced sounds indicate pain, such as moaning, crying, screaming, and the like.

According to an embodiment, the determining the pain indicator, by the processing unit 130, is further based on the biosignal data. In an embodiment, the determining the pain indicator is further based on a predetermined correlation between an amount of change in the one or more biosignals and the subject experienced pain. That is, advantageously the present system 10 may be used to indicate the subject generating sound, and further to verify that the sound relates to experienced pain by the subject. Thus, subjects experiencing "fake" pain may be detected. For example, a patient may generate sound which is of high volume, but is not necessarily related to pain. The system 10 may utilize a predetermined (comprises also pre-set) correlation between certain biosignal(s) and experienced pain. For example, the system 10 may determine that the sound is not related to pain if change in the biosignal is not over a certain threshold (e.g. over certain percent or change rate is lower than a threshold).

It is additionally or alternatively possible, that the user interface 140 is configured to be used for inputting experienced pain level with a certain scale (e.g. pain level 1 to 10). That is, the subject may him/herself use the interface 140 to input his/her pain level with a subjective scale. In such case, the pain indicator may be determined additionally based on the subject input or solely based on the subject input. For example, the subject input (may be referred to as manual input) can be used, by the system 10, for calibration of measured pain level when sound pressure and/or volume and/or sound pitch and/or biosignal level is used for measuring pain. Calibration may mean, for example, that the experienced pain by the subject is determined based on a correlation between certain sound(s) generated by the subject and subject inputted pain indication. E.g. the subject may experience pain which is detected by the system as a sound having certain characteristics. The subject or some other person may use the user interface 140 to input subjective indication about the pain (e.g. pain level 5 out of 10). Hence, the system 10 may determine that said certain sound characteristic indicates certain pain level (e.g. in this case pain level 5), and may use this information later. In an embodiment, the system 10 prompts the subject to provide the manual input in case the system detects a sound exceeding the threshold.

In an embodiment, the system 10 (e.g. processing unit 130) is configured to generate an identifier about the person who inputs the manual input about the pain level. For example, the manual input may be provided by a caretaker (e.g. nurse or doctor) or by the subject (e.g. the patient). The system 10 can indicate and prioritize pain indication reliability based who inputs the pain level. For example doctor is prioritized higher than nurse and nurse is prioritized higher than a patient or parent. Pain input calibration can be made between these input person groups as well measured pain level. So the system can reliably handle different pain levels inputted by different persons.

It is further noted that the measured audio signal and/or the manual input (i.e. subjective pain indication) may be measured close or in touch to the subject and then sent to a cloud database (e.g. database 154 of FIG. 1). The system 10 may read and analyze data from a cloud service, and output different parameters and/or indications discussed above to/via the cloud service. User device, such as computer or mobile device, may be used to read and output the data (e.g. parameters and indications, such as indication about who produces sound and/or pain indicator) from said cloud service. Said user device may be the external device discussed above, for example. That is, the pain indicator and/or indication about the sound source may be transmitted by the system 10 via the TRX 160 to the user device, for example. In an embodiment, the system 10 comprises one or more said user devices. For example, the user device may be helpful for a doctor or nurse in a hospital environment.

According to yet another embodiment, the apparatus (e.g. processing unit 130) carrying out the embodiments comprises a circuitry including at least one processor and at least one memory including computer program code (as described, the memory may also be external to the processing unit 130). When activated, the circuitry causes the apparatus to perform at least some of the functionalities according to any one of the embodiments of FIGS. 1 to 5D, or operations thereof.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware.

In an embodiment, at least some of the processes described in connection with FIGS. 1 to 5D may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, antenna, antenna circuitry, and circuitry. In an embodiment, the at least one processor, the memory, and the computer program code form processing means or comprises one or more computer program code portions for carrying out one or more operations according to any one of the embodiments of FIGS. 1 to 5D or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described in connection with FIGS. 1 to 5D may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

The invention claimed is:

1. A system for determining a sound source, the system comprising:
    an audio sensor;
    a plurality of biosensors configured to measure one or more biosignals of, and configured to be associated with, a plurality of subjects; and
    a processor communicatively coupled with the audio sensor and the biosensors, the processor being configured to perform operations comprising:
    obtaining audio data from the audio sensor and biosignal data from the biosensors, the audio data and the biosignal data being time-synced with each other,
    detecting, based on the audio data, a sound exceeding a threshold, and
    determining that the sound exceeding the threshold originates from the subjects if the biosignal data indicates a change in the one or more biosignals at a corresponding time, and identifying the one of the subjects as generating sound based on the biosignal data obtained from the plurality of biosensors.

2. The system of claim 1, wherein the processor is configured to perform further operations comprising generating for output an indication identifying a given subject, provided that sound exceeding the threshold is determined to originate from the given subject.

3. The system of claim 1, wherein the processor is configured to perform further operations comprising:
determining, based on at least one predetermined criterion and the sound exceeding the threshold, a pain indicator for indicating subject experienced pain, and
generating output including the pain indicator.

4. The system of claim 3, wherein the pain indicator is determined based on a predetermined correlation between at least one characteristic of sound and subject experienced pain.

5. The system of claim 4, wherein the at least one characteristic of sound comprises sound pressure, the pain indicator being determined based on a predetermined correlation between the sound pressure and the subject experienced pain.

6. The system of claim 3, wherein the determining of the pain indicator is further based on the biosignal data.

7. The system of claim 6, wherein the determining of the pain indicator is further based on a predetermined correlation between an amount of change in the one or more biosignals and the subject experienced pain.

8. The system of claim 1, wherein the biosignal data comprises heart rate data.

9. The system of claim 1, wherein the biosignal data comprises heart rate variation data.

10. The system of claim 1, wherein the biosignal data comprises respiration rate data.

11. The system of claim 1, wherein the processor is configured to perform further operations comprising determining that the sound exceeding the threshold originates from the subjects only if the biosignal data indicates a change at the corresponding time in at least two of the following biosignals: heart rate, heart rate variation, and respiration rate.

12. The system of claim 1, further comprising:
a body at least partially enclosing the audio sensor and the biosensor.

13. The system of claim 1, further comprising:
a data store configured to store audio data and/or biosignal data; and
a server configured to obtain the stored data, the server comprising the processor.

14. A method for determining a sound source, the method comprising:
obtaining, by a processor, audio data from an audio sensor and biosignal data from a plurality of biosensors, the biosensors being configured to measure one or more biosignals of, and configured to be associated with, a plurality of subjects, the audio data and the biosignal data being time-synced with each other;
detecting, based on the audio data, a sound exceeding a threshold; and
determining that the sound exceeding the threshold originates from the subjects if the biosignal data indicates a change in one or more of the biosignals at a corresponding time, and identifying the one of the subjects as generating sound based on the biosignal data obtained from the plurality of biosensors.

15. The method of claim 14, further comprising:
determining, based on at least one predetermined criterion and the sound exceeding the threshold, a pain indicator for indicating subject experienced pain; and
generating output including the pain indicator.

16. The method of claim 15, wherein the pain indicator is determined based on a predetermined correlation between at least one characteristic of sound and subject experienced pain.

17. The method of claim 16, wherein the at least one characteristic of sound comprises sound pressure, the pain indicator being determined based on a predetermined correlation between the sound pressure and the subject experienced pain.

18. The method of claim 15, wherein the determining of the pain indicator is further based on the biosignal data.

19. The method of claim 17, wherein the determining of the pain indicator is further based on a predetermined correlation between an amount of change in the one or more biosignals and the subject experienced pain.

20. The method of claim 14, further comprising determining that the sound exceeding the threshold originates from the subjects only if the biosignal data indicates a change at the corresponding time in at least two of the following biosignals: heart rate, heart rate variation, and respiration rate.

* * * * *